(12) United States Patent
Von Hollen et al.

(10) Patent No.: US 9,364,621 B2
(45) Date of Patent: Jun. 14, 2016

(54) VALVED HOLDING CHAMBER INCLUDING VALVE RETENTION SYSTEM

(75) Inventors: Dirk Ernest Von Hollen, Clark, NJ (US); Ashwin Kumar Kumar Viswanath, Randolph, NJ (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 351 days.

(21) Appl. No.: 13/825,253

(22) PCT Filed: Sep. 14, 2011

(86) PCT No.: PCT/IB2011/054020
§ 371 (c)(1),
(2), (4) Date: Mar. 20, 2013

(87) PCT Pub. No.: WO2012/038861
PCT Pub. Date: Mar. 29, 2012

(65) Prior Publication Data
US 2013/0186393 A1    Jul. 25, 2013

Related U.S. Application Data

(60) Provisional application No. 61/384,741, filed on Sep. 21, 2010.

(51) Int. Cl.
*A61M 15/00* (2006.01)
*A61M 11/04* (2006.01)
*A61M 16/20* (2006.01)

(52) U.S. Cl.
CPC ........... *A61M 15/0086* (2013.01); *A61M 11/04* (2013.01); *A61M 15/0016* (2014.02);

(Continued)

(58) Field of Classification Search
CPC ............ A61M 15/00; A61M 15/0001; A61M 15/0013; A61M 15/0016; A61M 15/0018; A61M 15/0021; A61M 15/0025; A61M 15/0086; A61M 16/208; A61M 2205/0233
USPC ............ 128/200.14, 200.22, 200.23, 203.12, 128/203.15, 203.23, 203.24, 205.24
See application file for complete search history.

(56) References Cited

U.S. PATENT DOCUMENTS

| | | |
|---|---|---|
| 4,470,412 A | 9/1984 | Nowacki et al. |
| 4,809,692 A | 3/1989 | Nowacki et al. |

(Continued)

FOREIGN PATENT DOCUMENTS

| | | |
|---|---|---|
| EP | 1358901 A2 | 11/2003 |
| WO | 0059565 A1 | 10/2000 |
| WO | 03097142 A1 | 11/2003 |

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

A valved holding chamber (2) includes a main chamber housing (49 and a mouthpiece assembly (6) removeably coupled to a first end of the main chamber housing, the mouthpiece assembly including a mouthpiece housing (24) having a mouthpiece portion (32) and a valve housing portion (30), a retaining ring (28) provided within and coupled to the valve housing portion, and a one-way inhalation valve (26) having an annular valve seat member (52), wherein the valve seat member is held between the retaining ring and an engagement surface of the valve housing portion. In one particular embodiment, a portion of the first end of the main chamber housing engages the bottom of the valve seat member and creates a seal between the main chamber housing and the one-way inhalation valve and between the one-way inhalation valve and the mouthpiece housing.

15 Claims, 11 Drawing Sheets

(52) U.S. Cl.
CPC ....... *A61M15/0018* (2014.02); *A61M 15/0025* (2014.02); *A61M 16/208* (2013.01); *A61M 2205/186* (2013.01); *A61M 2205/581* (2013.01)

(56) References Cited

U.S. PATENT DOCUMENTS

| | | | |
|---|---|---|---|
| 4,832,015 A | 5/1989 | Nowacki et al. | |
| 5,012,803 A | 5/1991 | Foley et al. | |
| 5,042,467 A * | 8/1991 | Foley | A61M 15/0086 128/200.14 |
| 5,385,140 A * | 1/1995 | Smith | A61M 15/0086 128/200.23 |
| 5,816,240 A * | 10/1998 | Komesaroff | A61M 15/0086 128/200.14 |
| 5,848,588 A * | 12/1998 | Foley | A61M 15/0086 128/200.14 |
| 5,848,599 A | 12/1998 | Todd | |
| 6,026,807 A * | 2/2000 | Puderbaugh | A61M 15/0086 128/200.14 |
| 6,325,061 B1 * | 12/2001 | Dagsland | A61M 15/00 128/203.12 |
| 6,345,617 B1 * | 2/2002 | Engelbreth | A61M 15/0086 128/200.18 |
| 6,435,177 B1 * | 8/2002 | Schmidt | A61M 15/0086 128/200.18 |
| 6,557,549 B2 * | 5/2003 | Schmidt | A61M 15/0086 128/200.24 |
| 7,201,165 B2 * | 4/2007 | Bruce | A61M 16/06 128/200.23 |
| 7,360,537 B2 * | 4/2008 | Snyder | A61M 15/0086 128/200.23 |
| 7,562,656 B2 * | 7/2009 | Gallem | A61M 15/0086 128/200.14 |
| 7,748,385 B2 * | 7/2010 | Lieberman | A61M 15/0086 128/203.11 |
| 8,517,009 B2 * | 8/2013 | Kakade | A61M 15/009 128/200.18 |
| RE45,068 E * | 8/2014 | Schmidt | A61M 15/0086 128/200.23 |
| 8,905,020 B2 * | 12/2014 | Eagle | A61M 15/0086 128/200.14 |
| 2002/0170557 A1 * | 11/2002 | Schmidt | A61M 16/06 128/200.23 |
| 2003/0029447 A1 * | 2/2003 | Vito | A61M 15/0086 128/200.23 |
| 2003/0226562 A1 | 12/2003 | Schmidt et al. | |
| 2004/0231665 A1 * | 11/2004 | Lieberman | A61M 15/0086 128/200.14 |
| 2006/0011196 A2 | 1/2006 | Gallem et al. | |
| 2011/0232636 A1 * | 9/2011 | Von Hollen | A61M 15/0086 128/202.13 |
| 2012/0042874 A1 * | 2/2012 | Gallem | A61M 15/0086 128/200.14 |
| 2012/0080028 A1 * | 4/2012 | Bruce | A61M 16/06 128/200.23 |
| 2012/0247460 A1 * | 10/2012 | Stenzler | A61M 15/0086 128/203.12 |
| 2013/0008436 A1 * | 1/2013 | Von Hollen | A61M 15/0086 128/200.14 |
| 2013/0291862 A1 * | 11/2013 | Eagle | A61M 15/0086 128/203.12 |
| 2015/0047635 A1 * | 2/2015 | Poree | A61M 15/0086 128/203.12 |
| 2015/0090256 A1 * | 4/2015 | Chung | A61M 15/002 128/202.21 |

* cited by examiner

VALVED HOLDING CHAMBER INCLUDING VALVE RETENTION SYSTEM

The present invention pertains to respiratory drug delivery systems, and, in particular, to a valved holding chamber having a valve retention system.

DESCRIPTION OF THE RELATED ART

It is well known to deliver a medication to a patient's respiratory system to treat a medical condition using a respiratory drug delivery apparatus. For example, a patient suffering from an acute asthmatic attack may use a respiratory drug delivery apparatus to deliver a bronchodilator, such as albuterol (salbutamol), in the form of a fine mist to the patient's respiratory system.

A conventional respiratory drug delivery apparatus often consists of a metered dose inhaler ("MDI") and a spacer or valved holding chamber. The MDI, also known simply as an "inhaler", includes a canister or nebulizer that contains the medication under pressure and a canister holder, also called a boot, which is typically "L" shaped. Although it is common for a patient to use the canister holder as a mouthpiece for receiving the aerosolized medication into their airway directly from the aerosol dispensing leg of the canister holder, this configuration may not optimize the mixing of the medication with the air because the aerosolized medication is injected directly into the airway. Without adequate mixing of the drug with the air, the medication may not be inhaled into the patient's lungs where it is effective, but instead may form as droplets that are deposited in the patient's mouth and swallowed without the desired medicinal effect.

To enhance mixing of the medication with air, it is known to provide a spacer, also commonly referred to as a valved holding chamber, which attaches to the aerosol dispensing end (the outlet end) of the canister holder. The spacer, which is typically a small hollow cylinder with a one-way valve at the downstream end, receives the aerosol from the canister and allows it to form into a fine mist for inhalation into the airway of the patient. Optionally, a mask may be provided at the end of the spacer opposite the MDI so that the patient can breath through his or her mouth to receive the medication. Examples of conventional valved holding chambers and associated components are shown in U.S. Pat. Nos. 4,470,412; 4,809,692; and 4,832,015 all to Nowacki et al.; U.S. Pat. No. 5,012,803 to Foley et al.; U.S. Pat. No. 5,042,467 to Foley; U.S. Pat. No. 5,385,140 to Smith, U.S. Pat. No. 5,848,599 to Foley et al., and U.S. Pat. No. 6,557,549 to Schmidt et al.

While the valved holding chambers described in these patents improve mixing of the medication with air, still further improvements in respiratory drug delivery apparatus design are desirable.

In one embodiment, a valved holding chamber is provided that includes a main chamber housing and a mouthpiece assembly removeably coupled to a first end of the main chamber housing, the mouthpiece assembly including a mouthpiece housing having a mouthpiece portion and a valve housing portion, a retaining ring provided within and coupled to the valve housing portion, and a one-way inhalation valve having an annular valve seat member, wherein the valve seat member is held between the retaining ring and an engagement surface of the valve housing portion. In one particular embodiment, a portion of the first end of the main chamber housing engages the bottom of the valve seat member and creates a seal between the main chamber housing and the one-way inhalation valve and between the one-way inhalation valve and the mouthpiece housing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 9:
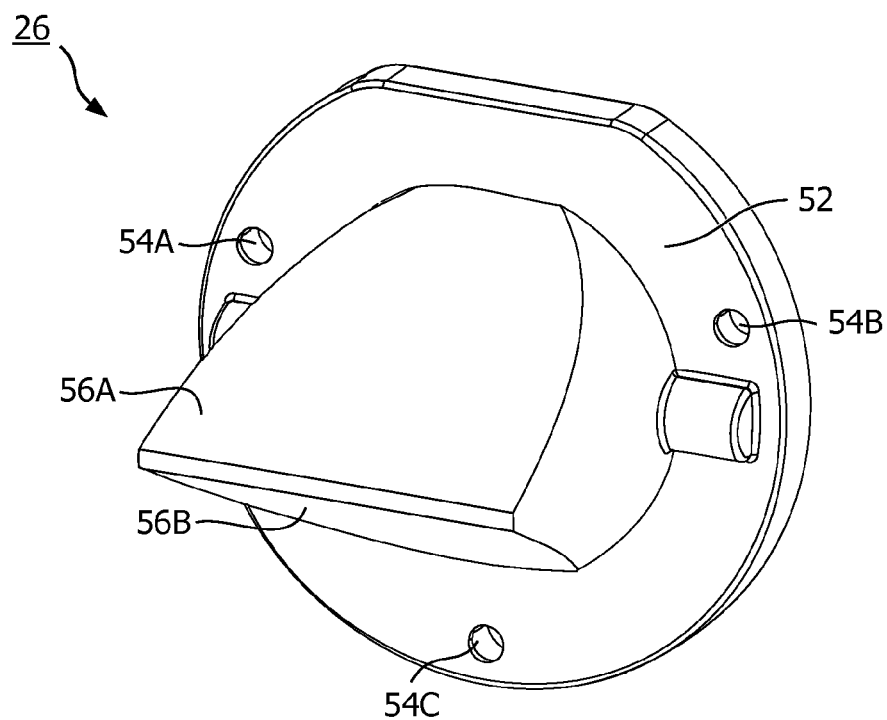
Figure 10:
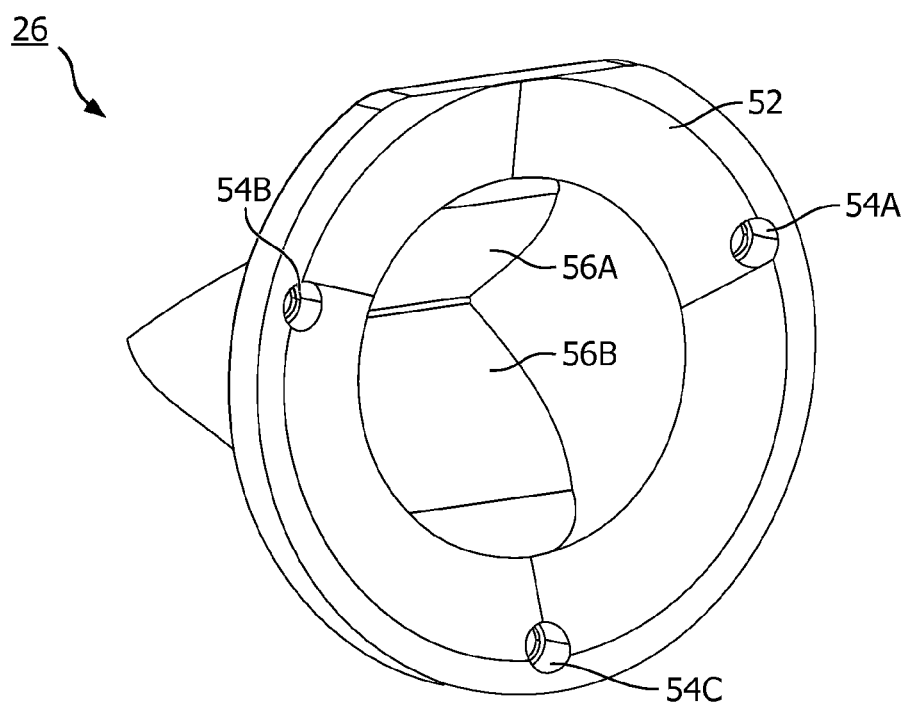
Figure 11:
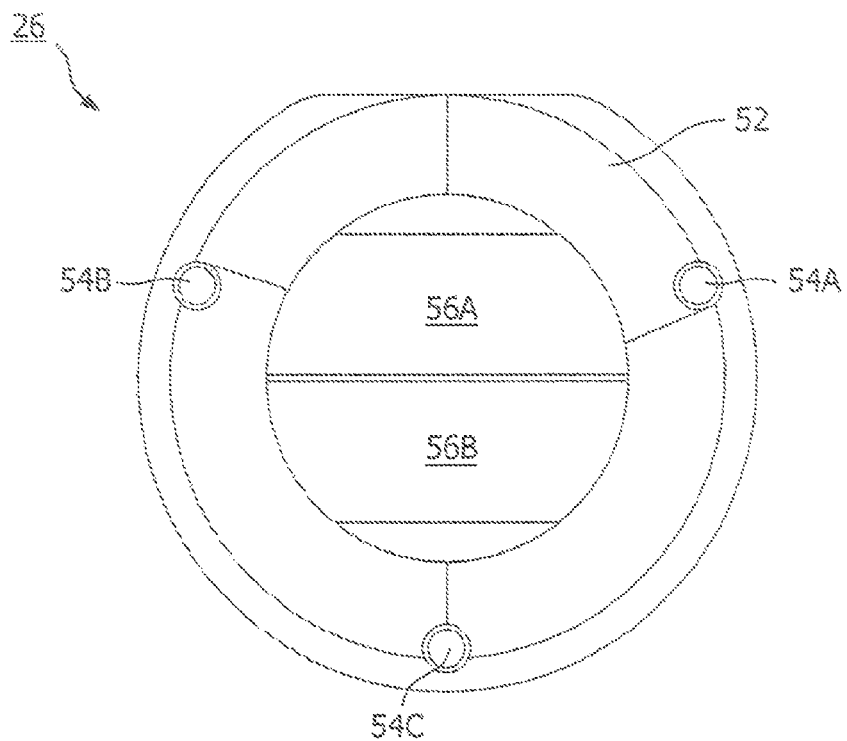
Figure 12:
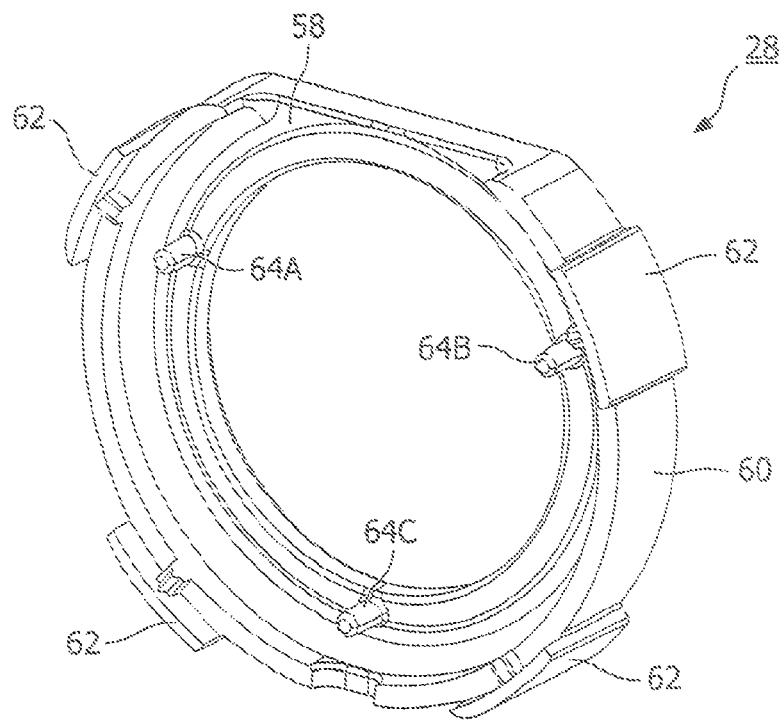
Figure 13:
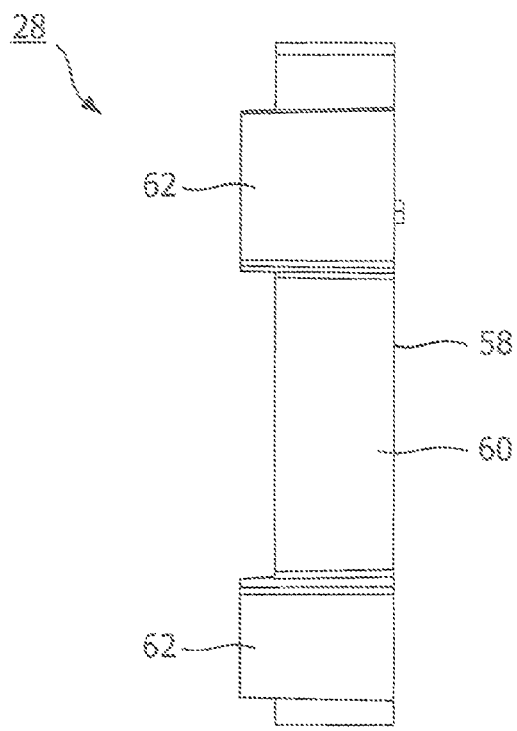
Figure 14:
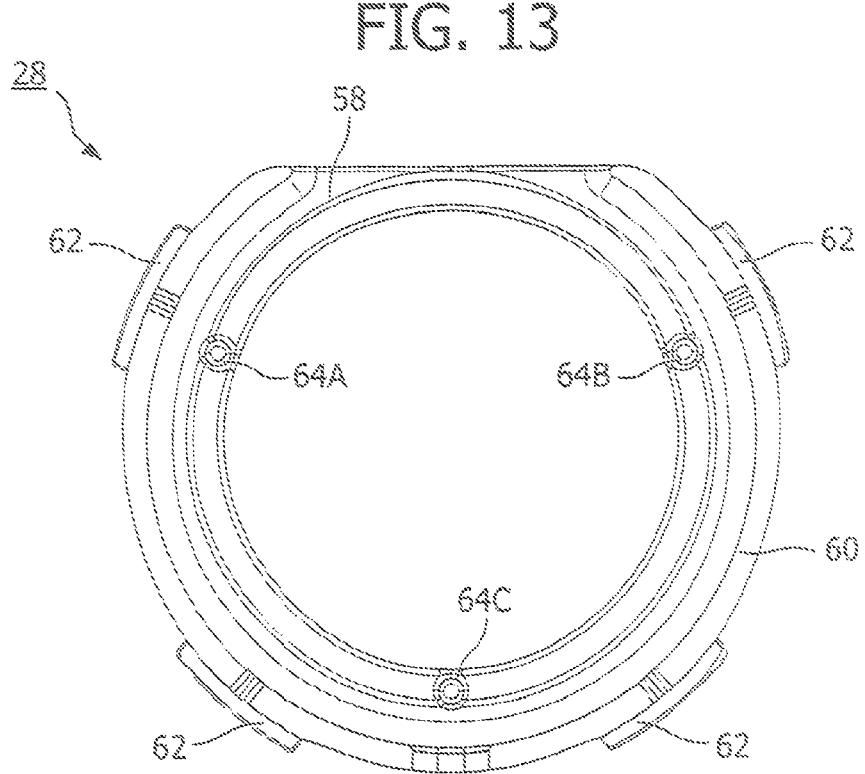
Figure 17:
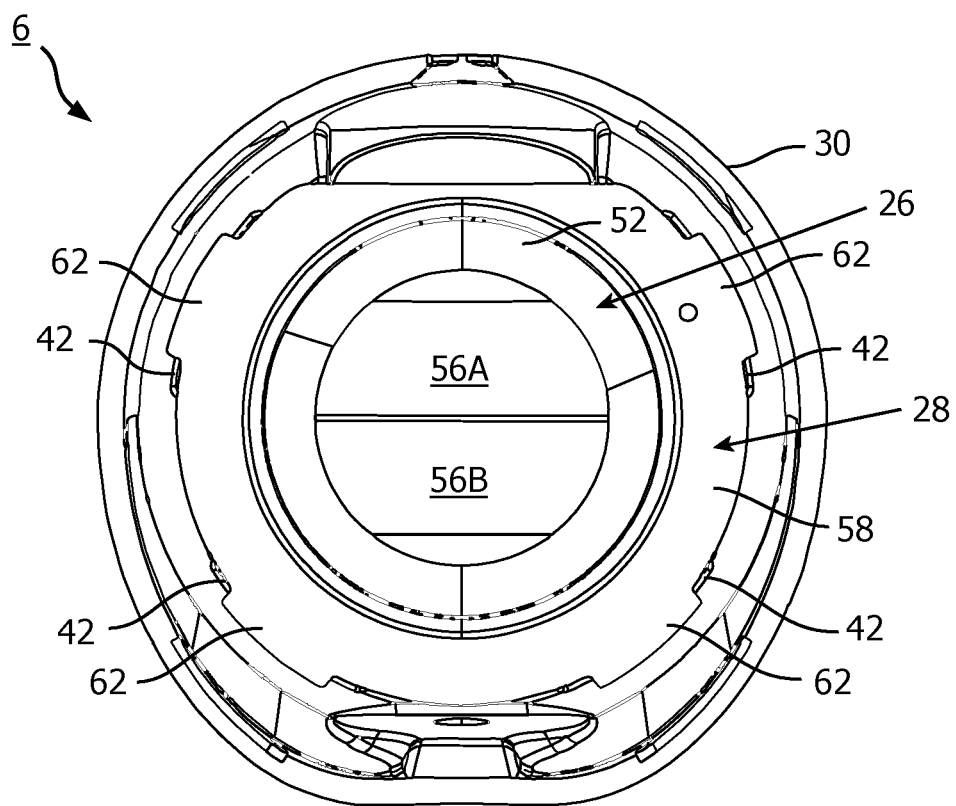
Figure 18:
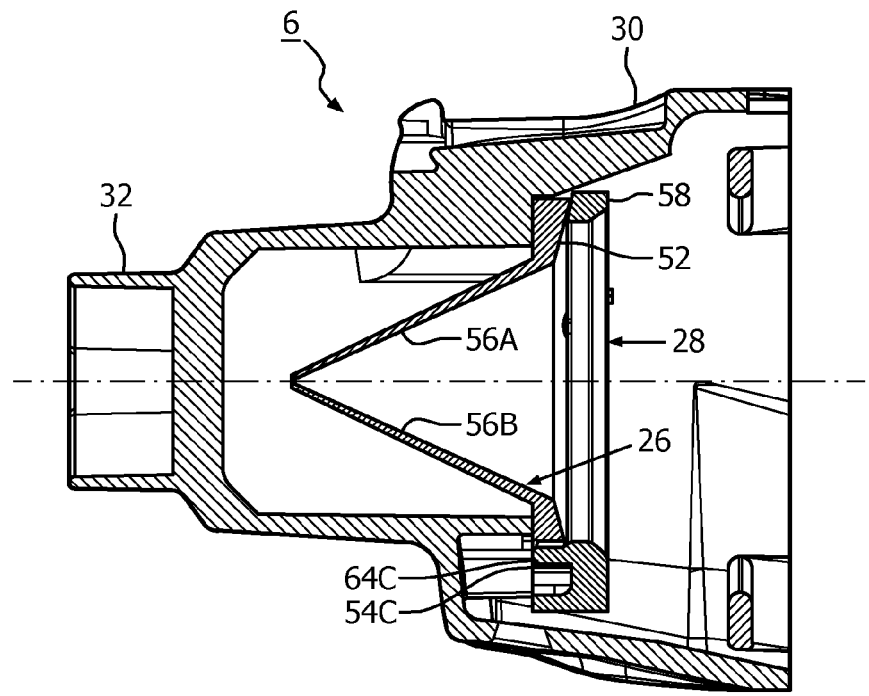
Figure 19:
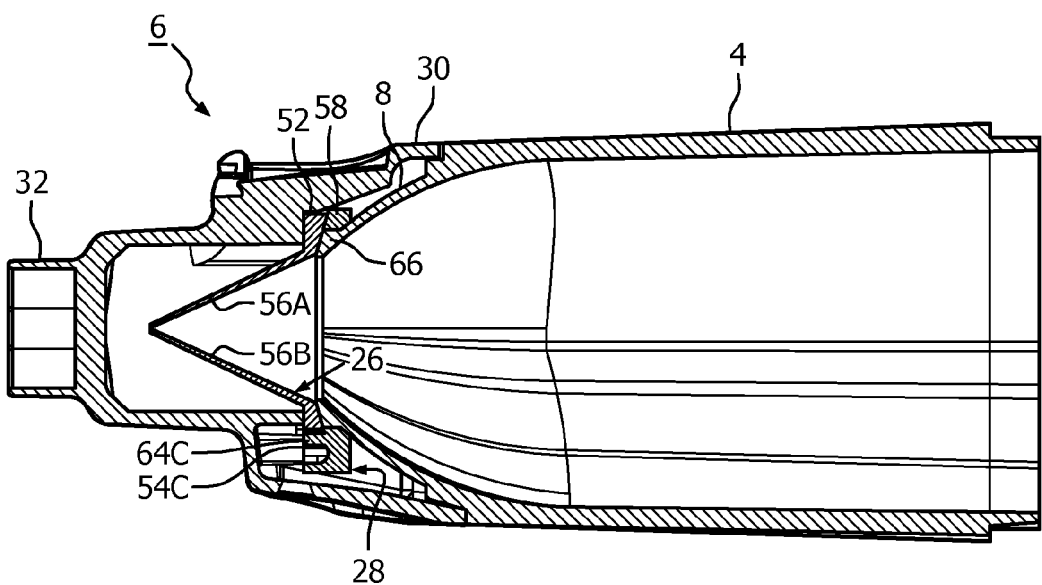

FIGS. 9, 10, and 11 are front isometric, rear isometric, and rear elevational views, respectively, of a duckbill valve forming a part of the valved holding chamber of FIGS. 1, 2, 3 and 4;

FIGS. 12, 13, and 14 are front isometric, side elevational, and front elevational views, respectively, of a retaining ring forming a part of the valved holding chamber of FIGS. 1, 2, 3 and 4;

FIGS. 15-18 illustrate how the mouthpiece assembly of the valved holding chamber of FIGS. 1, 2, 3 and 4 is assembled according to an exemplary embodiment of the present invention; and FIG. 19 is a cross-sectional diagram showing the main chamber housing connected to mouthpiece housing in the valved holding chamber of FIGS. 1, 2, 3 and 4.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

FIGS. 1, 2, 3 and 4 are front isometric, bottom, rear, and exploded views, respectively, of valved holding chamber 2 according to an exemplary embodiment of the present invention. Valved holding chamber 2 is structured to be used in connection with a metered dose inhaler (not shown) having a canister received within boot as described elsewhere herein. Valved holding chamber 2 includes generally cylindrical main chamber housing 4, that may be made of, for example and without limitation, an antistatic plastic material. In addition, mouthpiece assembly 6, described in greater detail elsewhere herein, is coupled to front end 8 of main chamber housing 4. Cap 10 is attached to the bottom of mouthpiece assembly 6, and is structured to be selectively attached to mouthpiece assembly 6 when valved holding chamber 2 is not in use.

Valved holding chamber 2 further includes two-part MDI adapter 12 that is structured to be removeably attached to second end 14 of main chamber housing 4. MDI adapter 12 is structured to receive and hold an MDI. MDI adapter 12 includes rigid end cap 16 made of, for example, a hard plastic or some other suitable rigid material that is structured to be selectively attachable to the rear end of main chamber 14. MDI adapter 12 further includes flexible inner portion 18 made of a flexible material, such as, without limitation, silicone, rubber, TPE, or foam, among other suitable materials. Inner portion 18 is structured to be received in and held by end cap 16 and may be made to be removable so that it can be cleaned and/or replaced if damaged, or, alternatively, may be permanently affixed to the end cap 16 by a process such as an over-molding process. Flexible inner portion 18 includes walls which define an aperture structured to the boot 12 of an MDI. The flexible nature of inner portion 18 enables it to hold MDIs of different shapes and sizes.

In addition, end cap 16 has an airflow actuated noisemaker 20 included therein, which in the illustrated embodiment is in the form of a whistle. Noisemaker 20 in the embodiment shown is a high airflow indicator that is structured to generate a noise when the air flowing through the main chamber housing 4 as a result of patient inhalation exceeding some predetermined level. Thus, noisemaker 20 provides a cautionary indication to the patient that the patient is inhaling too quickly and should slow down.

Figure 1:
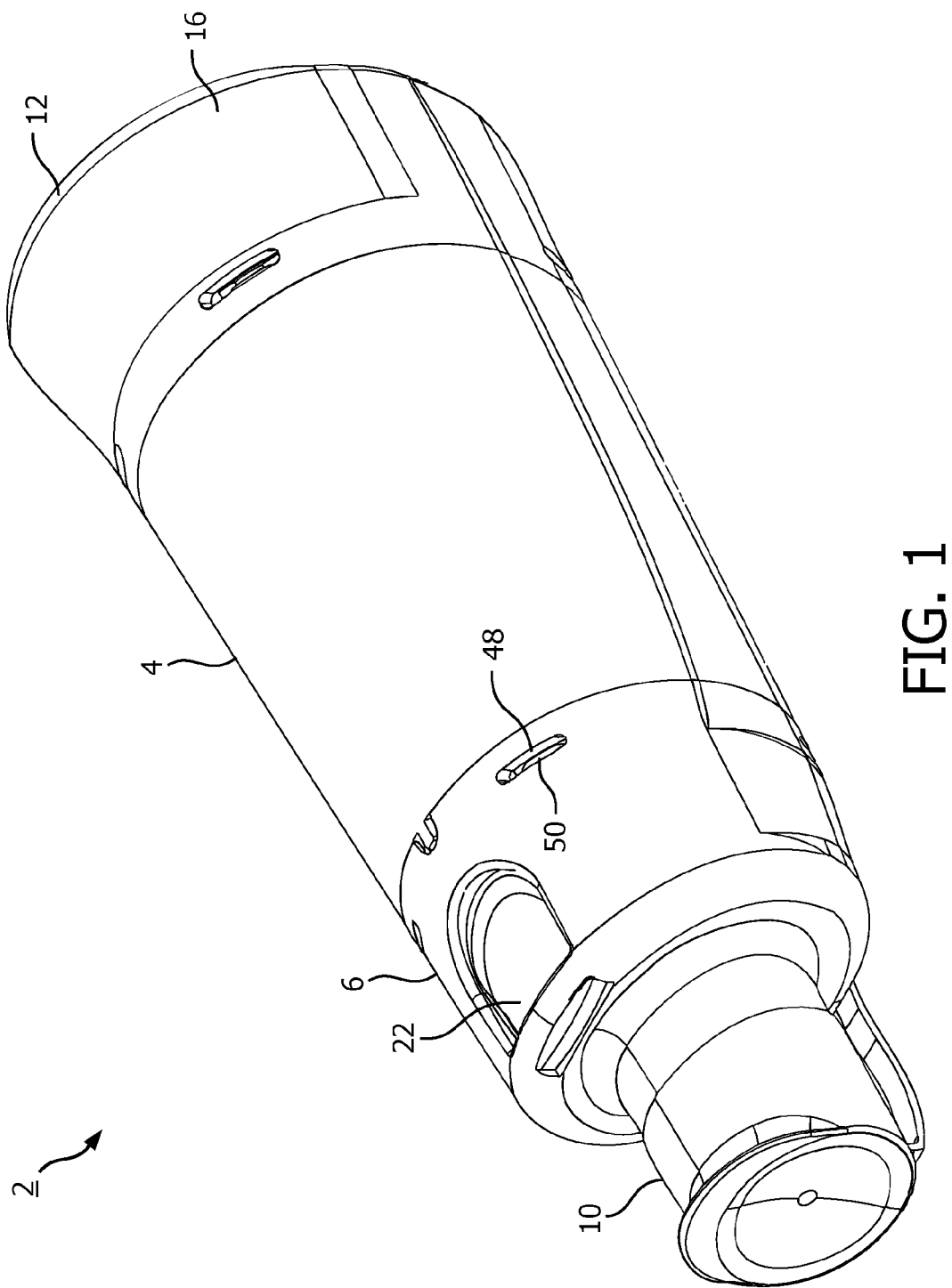
FIGS. 1, 2, 3 and 4 are front isometric, bottom, rear, and exploded views, respectively, of a valved holding chamber according to an exemplary embodiment of the present invention.
Figure 2:
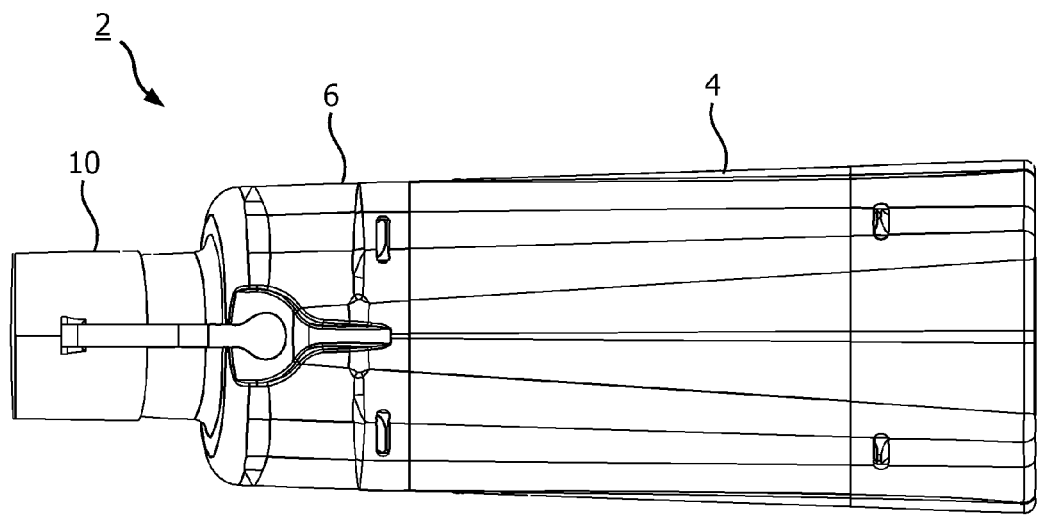
Figure 3:
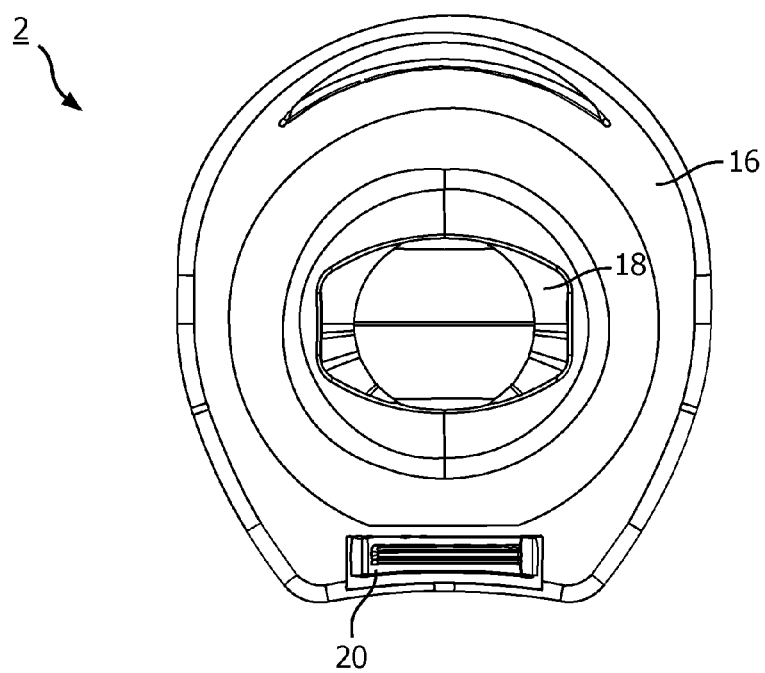
Figure 4:
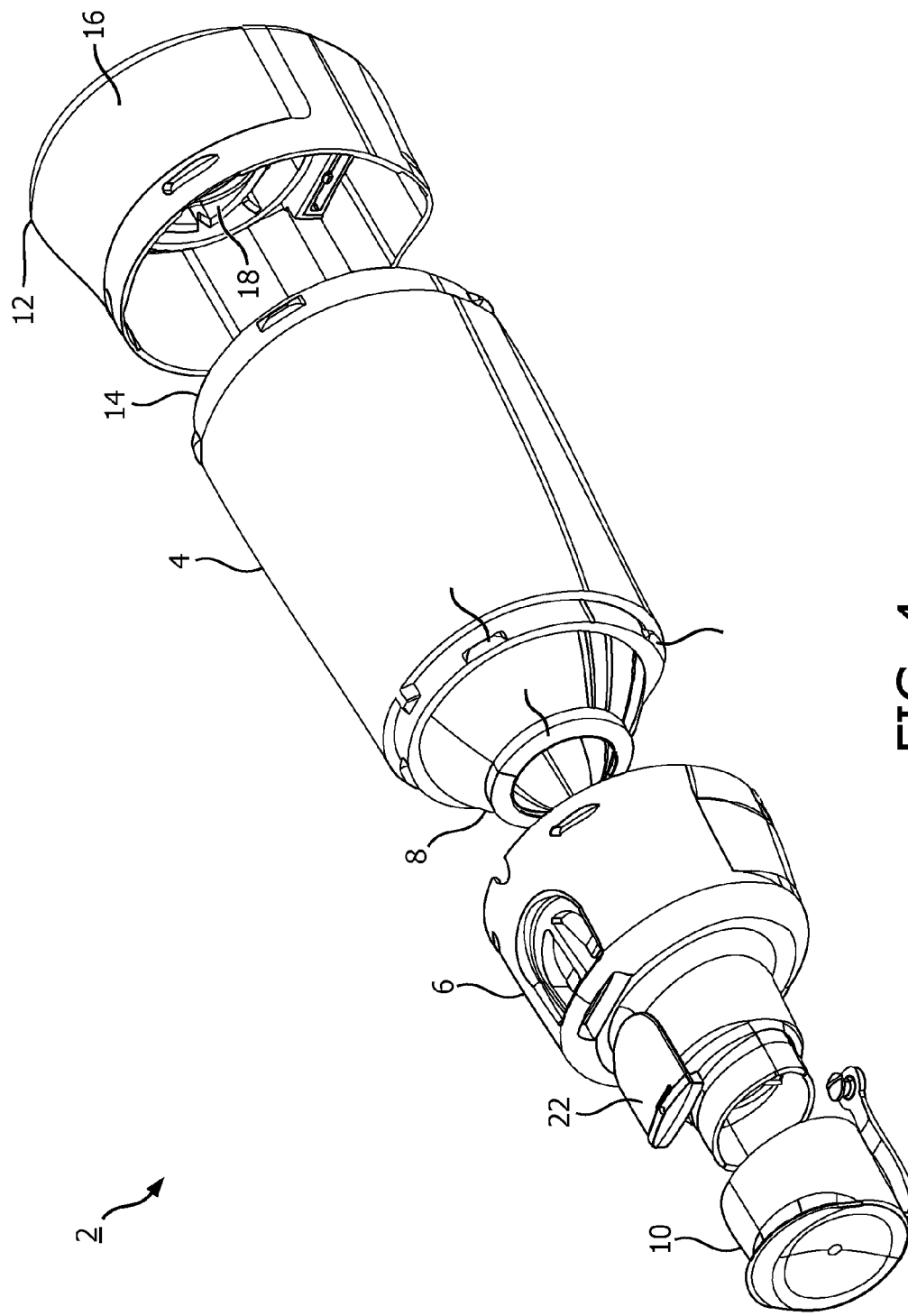

As seen in FIGS. 1 and 4, exhalation valve element 22 is operatively coupled to mouthpiece assembly 6 and is structured to allow exhaled gases to escape from valved holding chamber 2. In the illustrated embodiment, exhalation valve element 22 is in the form of a flap exhalation valve and is positioned on top of mouthpiece assembly 6 in a plane that is parallel or nearly parallel to the longitudinal axis of main chamber housing 4. In the exemplary, non-limiting embodiment, exhalation valve element 22 is positioned on top of mouthpiece assembly 6 in a plane that is at angle of five degrees with respect to a plane that is parallel to the longitudinal axis of main chamber housing 4. That orientation maximizes the visibility of exhalation valve element 22 by the patient while valved holding chamber 2 is being used so that the patient can monitor whether he or she is exhaling with the proper force, at the proper time, and/or for the proper duration.

Mouthpiece assembly 6 includes three components, mouthpiece housing 24, a one-way inhalation valve in the form of elastomeric duckbill valve 26 and retaining ring 28, each of which is described in greater detail below.

Figure 5:
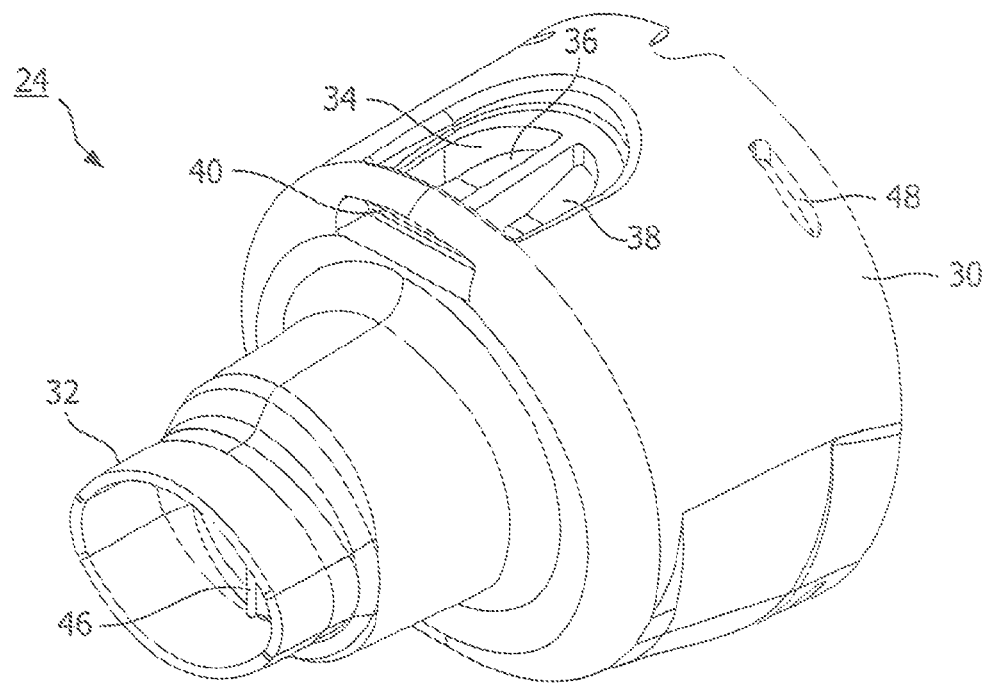
FIGS. 5, 6, 7 and 8 are front isometric, rear isometric, front elevational and rear elevational views, respectively, of a mouthpiece housing forming a part of the valved holding chamber of FIGS. 1, 2, 3 and 4.
Figure 6:
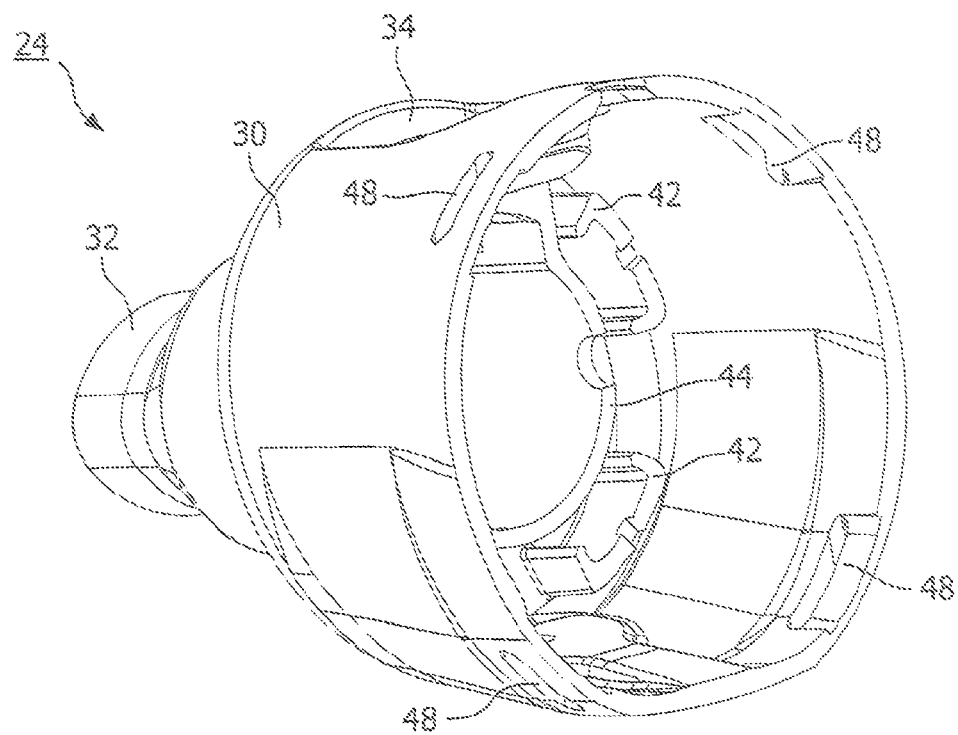
Figure 7:
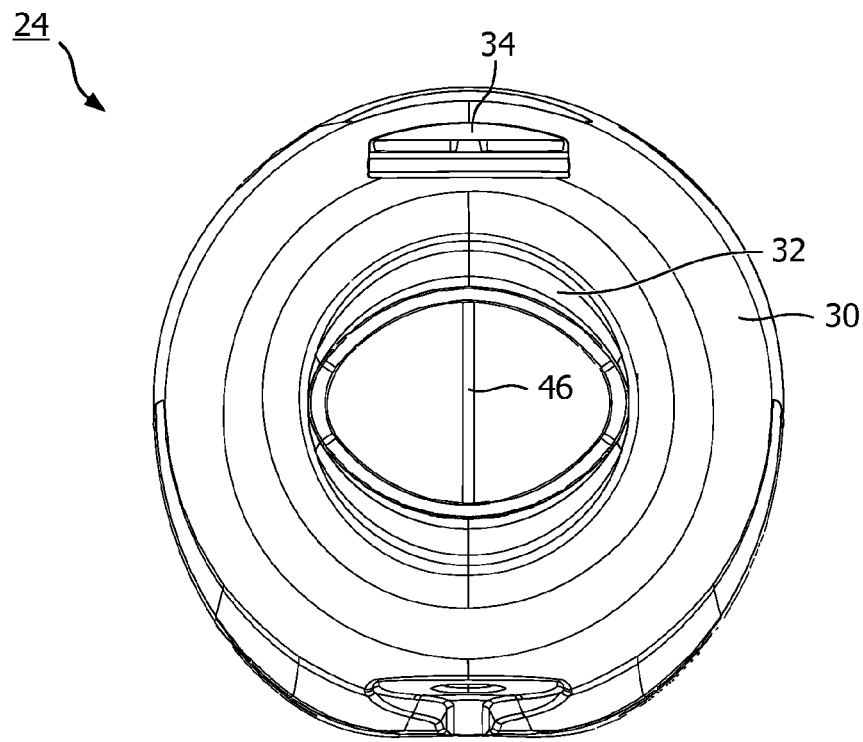
Figure 8:
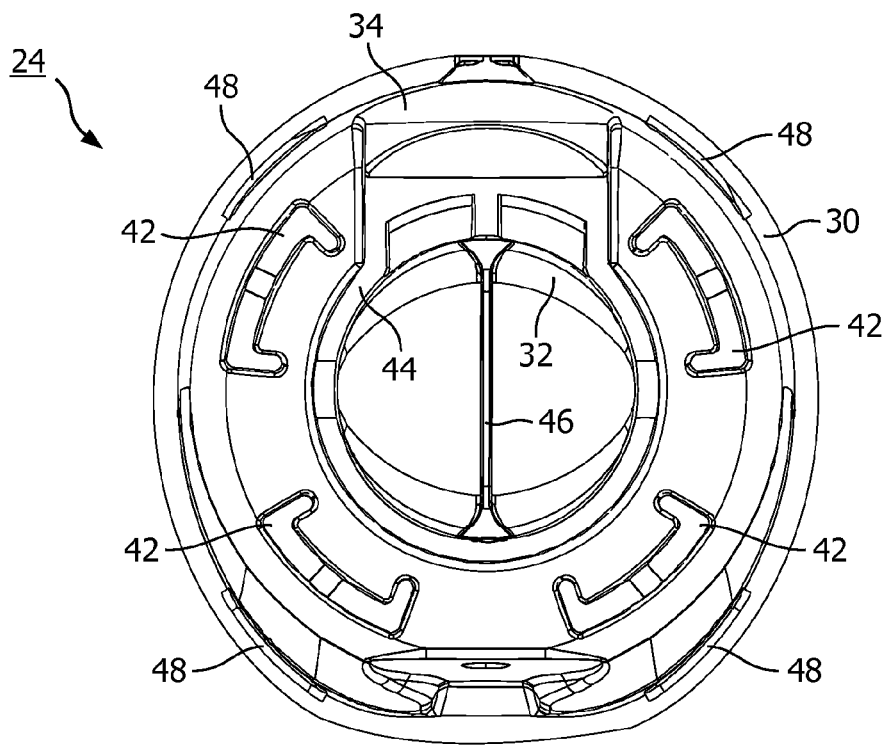

FIGS. 5, 6, 7 and 8 are front isometric, rear isometric, front elevational and rear elevational views, respectively, of mouthpiece housing 24. Mouthpiece housing 24 includes valve housing portion 30 coupled to mouthpiece portion 32 structured to be received within the lips of the patient during use of valved holding chamber 2. In the exemplary embodiment, mouthpiece housing 24 is made from an antistatic plastic material. Exhalation valve seat 34 for holding and retaining exhalation valve element 20 is provided on the top side of valve housing portion 30 and includes orifices 36 and 38 (i.e., exhalation ports) and slot 40 through which exhalation valve element 22 is inserted. The interior of valve housing portion 30 includes frames 42 and engagement surface 44, the purpose of which is described elsewhere herein. In addition, as seen in FIGS. 5, 7 and 8, the interior of mouthpiece portion 32 includes vertical bar 46, which act as a restraining element preventing an individual from inserting his or her fingers into the interior of mouthpiece assembly 6 through mouthpiece portion 32. Finally, valve housing portion 30 includes slots 48 which are structured to receive teeth 50 provided on the exterior of main chamber housing 4 in order to connect main chamber housing 4 and mouthpiece assembly 6 to one another.

FIGS. 9, 10, and 11 are front isometric, rear isometric, and rear elevational views, respectively, of duckbill valve 26. In the exemplary embodiment, duckbill valve 26 is made of an elastomeric material such as silicone rubber. Duckbill valve 26 includes valve seat member 52 having orifices 54A, 54B, 54C provided therein. Duckbill valve 26 also includes lips 56A, 56B extending upwardly from valve seat member 52.

FIGS. 12, 13, and 14 are front isometric, side elevational, and front elevational views, respectively, of retaining ring 28. In the exemplary embodiment, retaining ring 28 is made of an antistatic plastic material. Retaining ring 28 includes generally annular bottom wall 58 having generally annular outer wall 60 extending upwardly therefrom. Extension member 62 extend outwardly from outer wall 60. In addition, guideposts 64A, 64B, 64C are provided on bottom wall 58 and extend upwardly therefrom.

Figure 15:
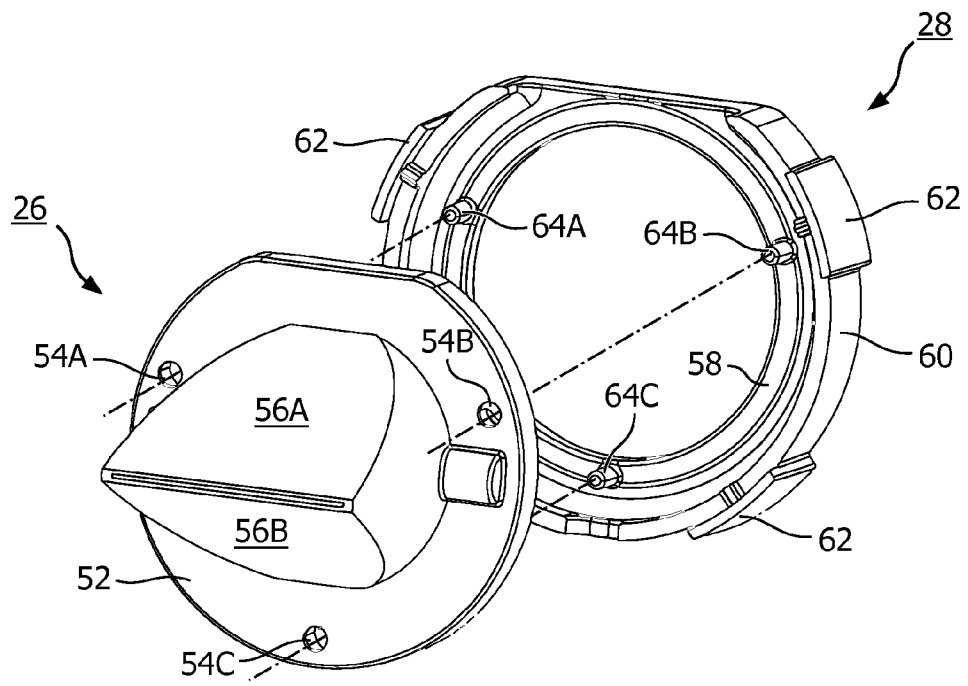
Figure 16:
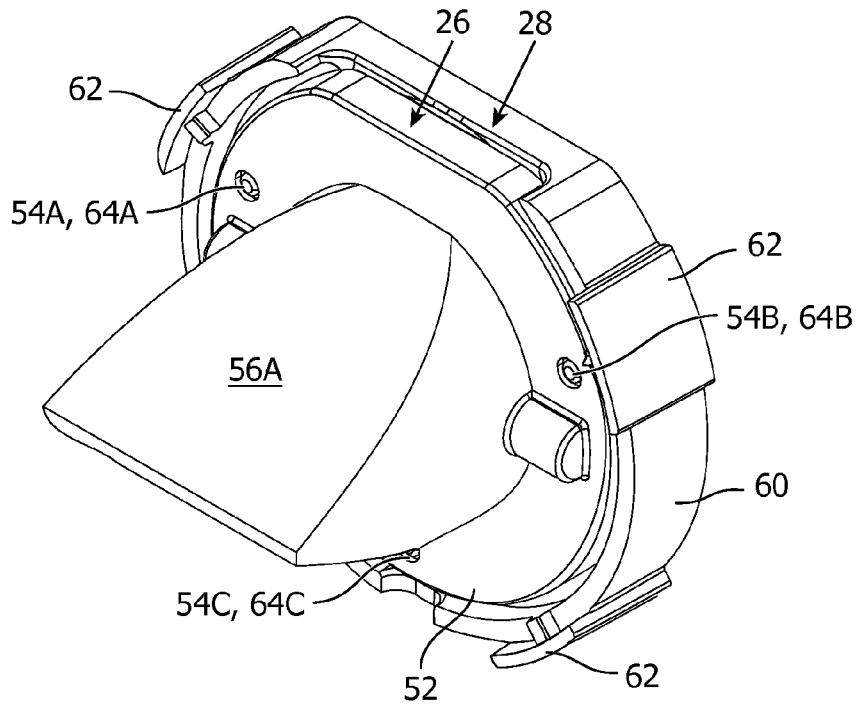

FIGS. 15-18 illustrate how mouthpiece assembly 6 is assembled according to an exemplary embodiment of the present invention. Referring to FIGS. 15 and 16, duckbill valve 26 is first coupled, to retaining ring 28 by inserting guideposts 64A, 64B, 64C through respective orifices 54A, 54B, 54C such that valve seat member 52 nests inside outer wall 60 and rests on bottom wall 58. Referring to FIGS. 17 and 18, the coupled duckbill valve 26 and retaining ring 28 are inserted into valve housing portion 30 of mouthpiece housing 24. In particular, each extension member 62 is inserted into a respective frame 42, where it is held by, for example, a friction fit or some other means such as a suitable adhesive. As seen in FIG. 18, valve seat member 52 is held between bottom wall 58 of retaining ring 28 and engagement surface 44 of valve housing portion 30.

Referring to FIG. 19, once mouthpiece assembly 6 is assembled as just described, main chamber housing 4 may be connected to mouthpiece assembly 6 by inserting teeth 50 into slots 48. As seen in FIGS. 4 and 19, front end 8 of main chamber housing 4 includes conically shaped/tapered edge 66. When main chamber housing 4 is connected to mouthpiece assembly 6 is just described, conically shaped edge 66 engages the bottom of valve seat member 52 (which is also conically shaped/tapered), compressing it and pushing it snugly against engagement surface 44, thereby producing a seal. Thereafter, the remaining components of valved holding chamber may be assembled as shown in FIGS. 1-4 and described elsewhere herein.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:
1. A valved holding chamber, comprising:
   a main chamber housing;
   a mouthpiece assembly removably coupled to a first end of the main chamber housing, the mouthpiece assembly including (a) a mouthpiece housing having (1) a mouthpiece portion and (2) a valve housing portion, (b) a retaining ring removably provided within and coupled to the valve housing portion, and (c) a one-way inhalation valve having an annular valve seat member, wherein the valve seat member is held between the retaining ring and an engagement surface of the valve housing portion, and wherein the first end of the main chamber housing engages a surface of the valve seat member; and an adaptor removably coupled to the main chamber, wherein the adaptor includes a noisemaker configured to generate a noise when airflow within the main chamber exceeds a predetermined level.

2. The valved holding chamber according to claim 1, wherein the one-way inhalation valve is an elastomeric duckbill valve.

3. The valved holding chamber according to claim 1, wherein the retaining ring and the engagement surface are structured to exert a compressive force on the valve seat member when the mouthpiece assembly is coupled to the main chamber housing.

4. The valved holding chamber according to claim 1, wherein the surface of the valve seat member is a bottom of the valve seat member that engages a bottom wall of the retaining ring, wherein the first end of the main chamber housing engages the bottom of the valve seat member and creates a seal between the main chamber housing and the one-way inhalation valve and between the one-way inhalation valve and the mouthpiece housing.

5. The valved holding chamber according to claim 4, wherein the portion of the first end of the main chamber housing is a tapered edge, and wherein the bottom of the valve seat member is tapered.

6. The valved holding chamber according to claim 1, wherein the retaining ring includes a generally annular bottom wall and a generally annular outer wall, wherein the valve seat member is nested within the outer wall and includes a bottom that engages the bottom wall.

7. The valved holding chamber according to claim 6, wherein the valve seat member includes a plurality of orifices, wherein the bottom wall includes a plurality of guideposts, and wherein each of the guideposts is received through a respective one of the orifices.

8. The valved holding chamber according to claim 6, wherein the valve housing portion includes a plurality of frame members, wherein the outer wall includes a plurality of extension members, and wherein each of the extension members is received within a respective one of the frame members.

9. The valved holding chamber according to claim 1, wherein the mouthpiece portion includes an internal restraining element restricting access to an interior of the mouthpiece assembly through the mouthpiece portion.

10. The valved holding chamber according to claim 9, wherein the internal restraining element is a bar extending from a first side of the interior of the mouthpiece portion to a second side of the interior of the mouthpiece portion.

11. The valved holding chamber according to claim 1, wherein the mouthpiece housing is made from an antistatic plastic material.

12. The valved holding chamber according to claim 11, wherein the retaining ring is made from an antistatic plastic material.

13. The valved holding chamber according to claim 1, wherein the mouthpiece housing includes an exhalation port provided on a top side thereof and a exhalation flap valve operatively coupled to the exhalation port, wherein the exhalation flap valve is structured to be positioned in a line of sight of a user when mouthpiece portion is inserted into a mouth of the user.

14. The valved holding chamber according to claim 1, wherein the first end of the main chamber housing includes a plurality of teeth, and wherein the valve housing portion includes a plurality of slots configured to receive the plurality of teeth.

15. The valved holding chamber according to claim 1, wherein the first end of the main chamber housing includes a conically shaped edge and wherein the conically shaped edge of the first end of the main chamber housing engages the surface of the valve seat member.

\* \* \* \* \*